US00PP14415P39

(12) United States Plant Patent
Moser

(10) Patent No.: US PP14,415 P3
(45) Date of Patent: Dec. 23, 2003

(54) CHRYSANTHEMUM PLANT NAMED 'MOZA CAN 01'

(50) Latin Name: *Chrysanthemum morifolium*
Varietal Denomination: Moza Can 01

(75) Inventor: Frank Moser, Alva, FL (US)

(73) Assignee: Mozant, LLC, Oxnard, CA (US)

( * ) Notice: Subject to any disclaimer, the term of this patent is extended or adjusted under 35 U.S.C. 154(b) by 0 days.

(21) Appl. No.: 09/865,149

(22) Filed: May 24, 2001

(65) Prior Publication Data

US 2002/0188976 P1 Dec. 12, 2002

(51) Int. Cl.[7] ..... A01H 5/00
(52) U.S. Cl. ..... Plt./286

(58) Field of Search ..... Plt./287, 289, 291, Plt./286

(56) References Cited

PUBLICATIONS

"Chrysanthemum Leaf Classification", http:www.ee.surrey-.ac.uk/Research/VSSP/demos/leaf/index.html, Jan. 2001.*

* cited by examiner

*Primary Examiner*—Anne Marie Grunberg
(74) *Attorney, Agent, or Firm*—Knobbe, Martens, Olson & Bear, LLP

(57) ABSTRACT

A new and distinct Chrysanthemum plant variety characterized by a decorative type inflorescence with pink and yellow colored ray florets, flexible plant habit, vigorous growth habit, and consistent natural season flowering habit during late September.

2 Drawing Sheets

Latin name of the genus and species of the plant claimed: *Chrysanthemum morifolium.*
Variety denomination: 'Moza Can 01'.

BACKGROUND OF THE INVENTION

The present invention relates to a new and distinct cultivar of Chrysanthemum plant, herein after referred to by the cultivar name 'Moza Can 01.'

This new cultivar originated from hybridization of a female parent Chrysanthemum cultivar MZ 215-01 (unpatented in the United States, and undistributed commercially) with a male parent Chrysanthemum cultivar MZ 257-01 (unpatented in the United States, and undistributed commercially). The new cultivar was discovered by the inventor in November 1998.

Asexual reproduction of the new cultivar by apical tip cutting and meristem tissue culture was performed in Oxnard, Calif. and has shown that the unique features of this new cultivar are stable and reproduced true to type on successive generations.

SUMMARY OF THE INVENTION

The cultivar 'Moza Can 01' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'Moza Can 01.' These characteristics in combination distinguish 'Moza Can 01' as a new and distinct Chrysanthemum:

1. Small, decorative type inflorescence;
2. Unique pink/yellow ray floret coloration;
3. Small foliage;
4. Compact growth habit; and 5. Consistent natural season flowering habit during late September.

Plants of the new cultivar are similar to plants of the female parent cultivar in most horticultural characteristics, however plants of the new cultivar differed from plants of the female parent cultivar in the following characteristics:

1. The new cultivar has different color ray florets;
2. The new cultivar is shorter;
3. The new cultivar has a different type bloom; and
4. The new cultivar has shorter internode length.

Plants of the new cultivar are similar to plants of the male parent cultivar in most horticultural characteristics, however plants of the new cultivar differed from plants of the male parent cultivar in the following characteristics:

1. The new cultivar has different color ray florets;
2. The new cultivar has a smaller diameter bloom; and
3. The new cultivar has shorter internode length.

BRIEF DESCRIPTION OF THE PHOTOGRAPHS

DETAILED BOTANICAL DESCRIPTION

Figure 1:
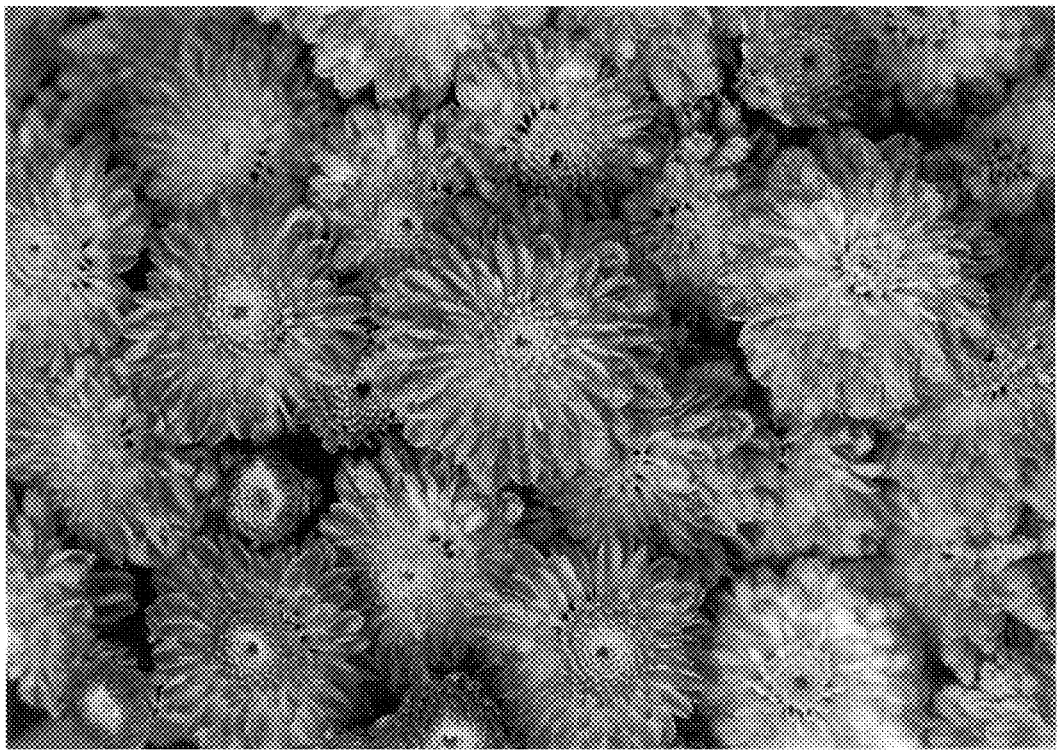
FIG. 1 shows a close up view of the flowers and buds of the new cultivar.
Figure 2:
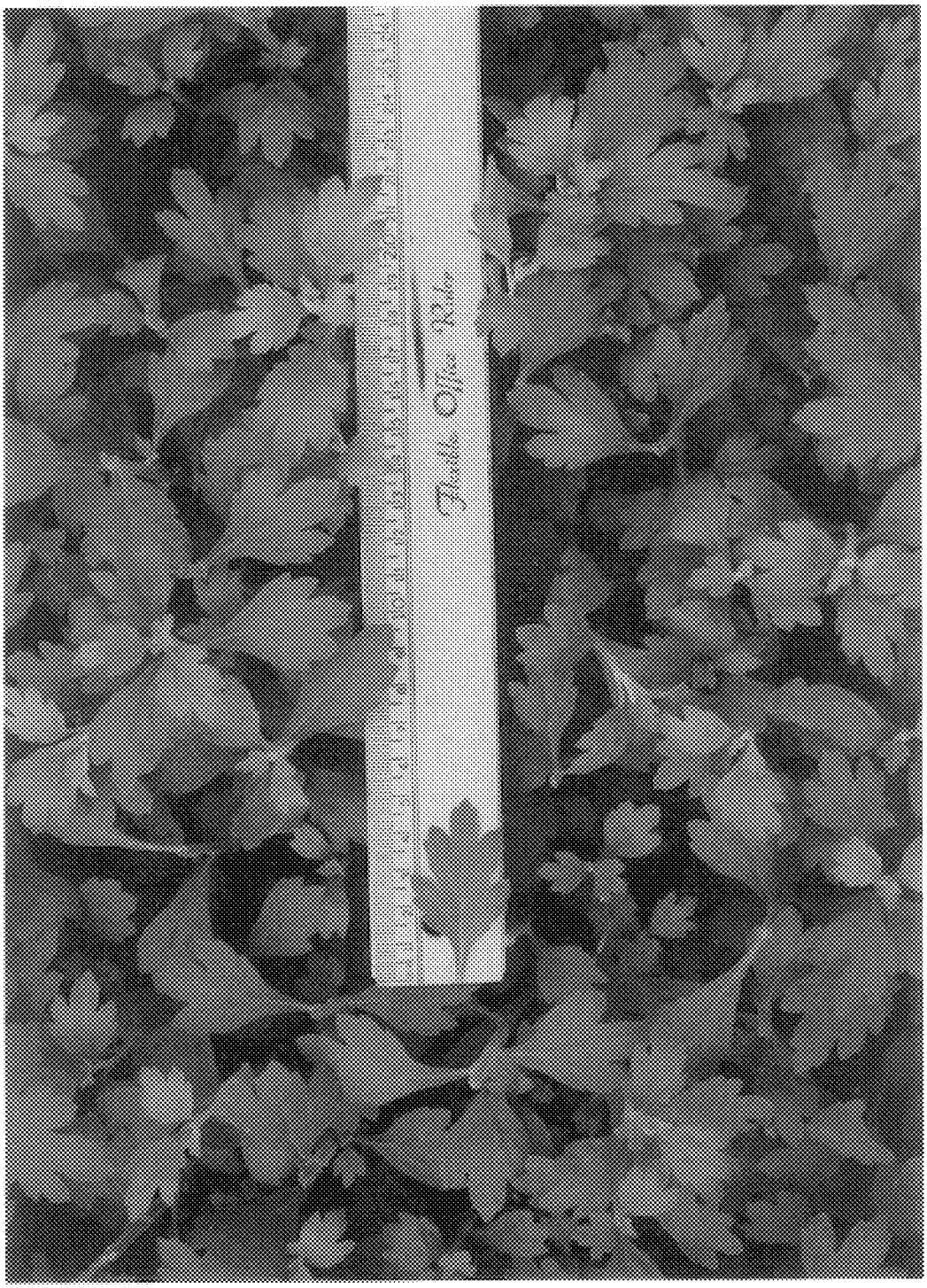
FIG. 2 shows the foliage of the new cultivar.

In the following description, color references are made to The Royal Horticultural Society Colour Chart except where general terms of ordinary dictionary significance are used. The following observations and measurements describe plants grown in a commercial field in Oxnard, Calif. in the month of September 2000. The plant described is approximately 90 days old, and was grown from a rooted cutting given one pinch after 10 days from planting. There was no spray or disbud treatment given. The growing conditions range from 60° to 65° F. at night to 70° to 85° during the day. Measurements and numerical values represent averages of typical flowering types.

Botanical classification: *Chrysanthemum morifolium* cultivar 'Moza Can 01'.

Commercial classification: Garden-type Chrysanthemum.

Parentage: Hybridization of female parent Chrysanthemum cultivar (unpatented in the United States) with a male parent Chrysanthemum cultivar (unpatented in the United States).

Commercial comparison: Comparison variety "Roadrunner" U.S. Plant Pat. No. 11,298, the most similar multi-color ray floret variety. The new variety differs from Roadrunner in having a later natural season bloom time, smaller diameter inflorescence, pink/yellow ray florets as opposed to red/yellow ray florets, more ray florets and less disc florets than Roadrunner.

PROPAGATION

Time to rooting: 7 to 14 days at approximately 21° C.

Rooting habit: Fine, fibrous.

PLANT

Growth habit: Mounding herbaceous perennial.

Height: Approximately 22 cm.

Branching characteristics: Free Branching.

Internode length: Approximately 2.1 cm.

Length of lateral branches: Approximately 18 cm.

Number of leaves per lateral branch: Approximately 15.

Stem color: Near 138B.

FOLIAGE

Leaf:

*Arrangement.*—Alternate single.

*Average length.*—Approximately 5.0 cm.

*Average width.*—Approximately 3.0 cm.

*Shape of blade.*—Ovate.

*Apex.*—Acuminate.

*Base.*—Attenuate.

*Attachment.*—Stalked.

*Margin.*—Serrate.

*Texture of top surface.*—Lightly pubescent.

*Texture of bottom surface.*—Lightly pubescent.

*Color.*—Young foliage upper side: Near 138A. Young foliage under side: Near 138A. Mature foliage upper side: Near 138A. Mature foliage under side: Near 138A. Venation upper side: Near 138B. Venation under side: Near 137B.

Petiole:

*Average length.*—Approximately 1.6 cm.

*Petiole color.*—Approximately 137A.

BLOOM

Inflorescence:

*Flowering habit.*—Induced by darkness period greater than 13.5 hours, blooming consistently after 49 days of appropriate day length required to induce and develop blooms.

*Inflorescence form.*—Decorative.

*Natural flowering season.*—Approximately the last two weeks in September.

*Number of inflorescences per stem.*—Approximately 16.

*Inflorescence diameter.*—Approximately 3.5 cm.

*Inflorescence depth.*—Approximately 2.5 cm.

*Inflorescence longevity on plant.*—Approximately 22 to 26 days.

*Persistence.*—Persistent.

*Fragrance.*—Not Present.

Ray florets:

*Appearance.*—Matte.

*Texture.*—Smooth.

*Average number per flower.*—Approximately 200.

*Shape.*—Oblanceolate.

*Margin.*—Entire.

*Apex.*—Acute.

*Length.*—Approximately 1.8 cm.

*Width.*—Approximately 0.5 cm.

*Color.*—Upper surface at first opening: Near 39A at the tip; Near 15C at the base. Upper surface at maturity: Near 46D at the tip; Near 40D at the base. Upper surface at fading: Near 37A at the tip; Near 24D at the base. Under surface at first opening: Near 13A. Under surface at maturity: Near 33C at the tip; Near 16D at the base. Under surface at fading: Near 33D at the tip; Near 20C at the base.

Disc florets:

*Appearance.*—Shiny.

*Texture.*—Smooth.

*Average number per flower.*—Approximately 20.

*Shape.*—Cylindric.

*Apex.*—Obtuse.

*Average length.*—Approximately 0.5 cm.

*Average width.*—Approximately 0.1 cm.

*Color.*—At first opening: Near 154B. At maturity: Near 4A. At fading: Near 7A.

Peduncle:

*Length.*—At terminal end (shortest): Approximately 4 cm. At lateral end (longest): Approximately 5.5 cm.

*Strength.*—Moderate.

*Color.*—Near 138A.

*Habit.*—Erect.

Inflorescence bud:

*Length.*—Approximately 0.9 cm.

*Diameter.*—Approximately 0.9 cm.

*Form.*—Globular.

*Color.*—Near 42B.

Sepals:

*Appearance.*—Matte.

*Texture.*—Lightly pubescent.

*Number.*—Approximately 20 to 30.

*Shape.*—Ovate.

*Margin.*—Entire.

*Apex.*—Acute.

*Color.*—Upper side: Near 137A. Under side: Near 137A.

REPRODUCTIVE ORGANS

Ray florets:

*Number of pistils per floret.*—1.

*Stigma shape.*—2 branched.

*Stigma color.*—Near 4A.

*Style color.*—Near 2D.

*Style length.*—Approximately 0.5 cm.

*Number of stamens per floret.*—Absent.

Disc florets:

*Number of pistils per floret.*—1.

*Stigma shape.*—Cylindric.

*Style length.*—Approximately 0.3 cm.

*Stigma color.*—Near 4D.

*Style color.*—Near 1D.

*Number of stamens per floret.*—Approximately 5.

*Anther shape.*—Tubular.
*Anther color.*—Near 5B.
*Pollen color.*—Near 5A.

OTHER CHARACTERISTICS

Seed production: Commercially, this plant is not used or observed in a stage wherein seeds would be produced. Therefore, seed production has not been observed.

Disease resistance: Neither resistance nor susceptibility to diseases and pests have been observed in this cultivar.

What is claimed is:

1. A new and distinct variety of Chrysanthemum plant named 'Moza Can 01' as herein illustrated and described.

* * * * *